(12) United States Patent
Robert et al.

(10) Patent No.: US 8,974,415 B2
(45) Date of Patent: Mar. 10, 2015

(54) FLOW STOP INSERT APPARATUS AND METHODS

(75) Inventors: Renee Robert, St. Paul, MN (US); Steve Cote, Stillwater, MN (US); Jeff Taylor, Forest Lake, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 232 days.

(21) Appl. No.: 13/443,390

(22) Filed: Apr. 10, 2012

(65) Prior Publication Data

US 2013/0267899 A1    Oct. 10, 2013

(51) Int. Cl.
*A61M 1/00*    (2006.01)

(52) U.S. Cl.
USPC ........................................................ 604/151

(58) Field of Classification Search
USPC ........................................................ 604/151
See application file for complete search history.

(56) References Cited

U.S. PATENT DOCUMENTS

| | | | |
|---|---|---|---|
| 3,494,458 A | | 2/1970 | Meierhoefer |
| 4,193,174 A | * | 3/1980 | Stephens ................. 24/532 |
| 4,381,836 A | | 5/1983 | Rivkin et al. |
| 4,451,693 A | | 5/1984 | Vest |
| 4,559,038 A | | 12/1985 | Berg et al. |
| 4,565,542 A | | 1/1986 | Berg |
| 4,567,983 A | | 2/1986 | Morris |
| 4,634,004 A | | 1/1987 | Mortensen |
| 4,650,469 A | | 3/1987 | Berg et al. |
| D294,733 S | | 3/1988 | Peterson et al. |
| 4,802,601 A | | 2/1989 | Pijanowski et al. |
| 4,867,738 A | | 9/1989 | Mintz |
| D309,662 S | | 7/1990 | Gorton |
| 4,944,485 A | * | 7/1990 | Daoud et al. ................. 251/9 |
| 5,017,192 A | | 5/1991 | Dodge et al. |
| 5,106,366 A | | 4/1992 | Steppe |
| 5,165,874 A | | 11/1992 | Sancoff et al. |

(Continued)

FOREIGN PATENT DOCUMENTS

| | | |
|---|---|---|
| EP | 1557187 | 7/2005 |
| EP | 2193815 A1 | 6/2010 |
| WO | WO00/51671 A1 | 9/2000 |

OTHER PUBLICATIONS

Search Report dated Jul. 23, 2013 for PCT Application No. PCT/US2013/035393, 10 pages.

(Continued)

*Primary Examiner* — Nicholas Lucchesi
*Assistant Examiner* — Diva K Chander
(74) *Attorney, Agent, or Firm* — Patterson Thuente Pedersen, P.A.

(57) ABSTRACT

An embodiment is directed to pressure plate for attachment to an infusion pump, where the pressure plate includes a tubing support surface at least partially surrounded by a raised perimeter support. The pressure plate includes a plurality of guide structures extending from the raised perimeter support that define a passageway for an infusion pump tube. Additionally an attachable flow stop assembly is included that includes an attachable occlusion arch and an attachable flow stop arm. The attachable occlusion arch includes a plurality of tab structures that couple to the raised perimeter support. The occlusion arch further includes an aperture configured to surround an infusion pump tube threaded therethrough. The attachable flow stop arm is operatively coupled to the raised perimeter support adjacent the attachable occlusion arch in a spring-biased fashion such that the aperture in the occlusion arch may be selectively occluded by the flow stop arm.

14 Claims, 7 Drawing Sheets

(56) References Cited

U.S. PATENT DOCUMENTS

| | | | | |
|---|---|---|---|---|
| 5,181,910 A | | 1/1993 | Scanlon | |
| 5,213,483 A | | 5/1993 | Flaherty et al. | |
| 5,257,978 A | * | 11/1993 | Haber et al. | 604/250 |
| 5,336,174 A | | 8/1994 | Daoud et al. | |
| 5,336,190 A | | 8/1994 | Moss et al. | |
| 5,364,242 A | | 11/1994 | Olsen | |
| D353,667 S | | 12/1994 | Tsubota et al. | |
| 5,370,622 A | | 12/1994 | Livingston et al. | |
| 5,397,222 A | | 3/1995 | Moss et al. | |
| 5,425,173 A | | 6/1995 | Moss et al. | |
| 5,429,485 A | | 7/1995 | Dodge | |
| 5,437,642 A | * | 8/1995 | Thill et al. | 604/153 |
| 5,453,098 A | | 9/1995 | Botts et al. | |
| 5,482,446 A | | 1/1996 | Williamson et al. | |
| 5,485,408 A | | 1/1996 | Bloomquist | |
| 5,531,697 A | | 7/1996 | Olsen et al. | |
| 5,531,698 A | | 7/1996 | Olsen | |
| 5,538,399 A | | 7/1996 | Johnson | |
| 5,540,561 A | | 7/1996 | Johnson | |
| 5,564,915 A | | 10/1996 | Johnson | |
| 5,567,119 A | | 10/1996 | Johnson | |
| 5,567,136 A | | 10/1996 | Johnson | |
| D376,848 S | | 12/1996 | Zeilig et al. | |
| 5,620,312 A | | 4/1997 | Hyman et al. | |
| 5,630,710 A | | 5/1997 | Tune et al. | |
| 5,647,854 A | | 7/1997 | Olsen et al. | |
| 5,658,252 A | | 8/1997 | Johnson | |
| 5,669,877 A | | 9/1997 | Bloomquist | |
| 5,695,473 A | | 12/1997 | Olsen | |
| 5,755,691 A | | 5/1998 | Hilborne | |
| 5,772,409 A | | 6/1998 | Johnson | |
| 5,782,805 A | | 7/1998 | Meinzer et al. | |
| 5,788,671 A | | 8/1998 | Johnson | |
| 5,788,674 A | | 8/1998 | McWilliams | |
| 5,810,771 A | | 9/1998 | Bloomquist | |
| 5,816,779 A | * | 10/1998 | Lawless et al. | 417/63 |
| 5,823,746 A | | 10/1998 | Johnson | |
| 5,879,143 A | | 3/1999 | Cote et al. | |
| 5,879,144 A | | 3/1999 | Johnson | |
| 5,904,668 A | | 5/1999 | Hyman et al. | |
| 5,928,196 A | | 7/1999 | Johnson et al. | |
| 5,935,099 A | | 8/1999 | Peterson et al. | |
| 5,935,106 A | | 8/1999 | Olsen | |
| 5,954,485 A | * | 9/1999 | Johnson et al. | 417/474 |
| 5,954,696 A | | 9/1999 | Ryan | |
| 5,993,420 A | | 11/1999 | Hyman et al. | |
| 6,024,539 A | | 2/2000 | Bloomquist | |
| 6,056,522 A | | 5/2000 | Johnson | |
| 6,059,753 A | * | 5/2000 | Faust et al. | 604/131 |
| 6,077,055 A | | 6/2000 | Vilks | |
| 6,123,686 A | | 9/2000 | Olsen et al. | |
| 6,131,773 A | | 10/2000 | Wade et al. | |
| 6,202,708 B1 | | 3/2001 | Bynum | |
| 6,203,528 B1 | | 3/2001 | Deckert et al. | |
| 6,241,704 B1 | | 6/2001 | Peterson et al. | |
| 6,267,564 B1 | | 7/2001 | Rapheal | |
| D447,558 S | | 9/2001 | Cartledge et al. | |
| 6,374,876 B2 | | 4/2002 | Bynum | |
| 6,422,057 B1 | | 7/2002 | Anderson | |
| 6,475,180 B2 | | 11/2002 | Peterson et al. | |
| 6,742,992 B2 | | 6/2004 | Davis | |
| 7,150,735 B2 | | 12/2006 | Hickle | |
| 7,258,534 B2 | | 8/2007 | Fathallah et al. | |
| 7,347,836 B2 | | 3/2008 | Peterson et al. | |
| D586,463 S | | 2/2009 | Evans et al. | |
| 7,654,976 B2 | | 2/2010 | Peterson et al. | |
| D626,647 S | | 11/2010 | Amborn et al. | |
| 7,967,773 B2 | * | 6/2011 | Amborn et al. | 604/19 |
| D655,810 S | | 3/2012 | Amborn et al. | |
| 2001/0010238 A1 | | 8/2001 | Bynum | |
| 2002/0183693 A1 | | 12/2002 | Peterson | |
| 2003/0014011 A1 | | 1/2003 | Robert | |
| 2008/0065007 A1 | | 3/2008 | Peterson et al. | |
| 2008/0065016 A1 | | 3/2008 | Peterson et al. | |
| 2008/0275425 A1 | | 11/2008 | Strickler et al. | |
| 2010/0094224 A1 | | 4/2010 | Fathallah et al. | |
| 2010/0211002 A1 | | 8/2010 | Davis | |
| 2011/0028899 A1 | | 2/2011 | Beck et al. | |
| 2011/0313358 A1 | | 12/2011 | Hariharesan et al. | |
| 2012/0330238 A1 | | 12/2012 | Robert et al. | |

OTHER PUBLICATIONS

Pressure plate and free-flow control for a CADD infusion pump cassette, as shown in Figs. 7A and 7B of the application, available prior to Apr. 10, 2012, 1 page.

* cited by examiner

Prior Art

*Fig. 7A*

Prior Art

FLOW STOP INSERT APPARATUS AND METHODS

FIELD OF THE INVENTION

The present invention relates to features for governing the flow of fluid in medical infusion pumps. More specifically, this invention relates to a flow stop insert for an infusion pump having an improved design for operation and manufacture.

BACKGROUND OF THE INVENTION

Infusion pumps, drug pumps and medication delivery devices are well-known and widely used throughout the world today. Intravenous infusion pumps were developed decades ago to pump fluid medicants or nutrients through a tube set to a patient in connection with treatment of a medical condition. Infusion pumps include peristaltic pumps, roller pumps, or expulsor pumps, for example. Various pumps include a reusable control module that is detachably coupled to a pressure plate on the top of a disposable or reusable fluid reservoir cassette. Fluid is pumped from the cassette by the reusable control module when the cassette is coupled to the control module. Alternatively, other variations of infusion pumps include a reusable pump control module and pressure plate cassette as part of an administration set that is used in conjunction with a remote IV bag or fluid reservoir which is separate from the pump control.

Infusion pumps operate by governing the movement of fluid through a delivery tube by selectively occluding portions of the tube by depressing a valve or mechanism against the tube. For example, in some pumps the mechanism of a pump selectively engages the tube against the pressure plate in a peristaltic fashion to force fluid through the tube.

In the past, one potentially problematic situation has been identified which is referred to as "free-flow". Free flow occurs in infusion pumps when fluid flows freely from the source of fluid through the tube into the patient. Medical personnel and pump operators try to avoid the occurrence of free-flow when administering fluids to patients.

Free-flow may cause serious harm to a patient due to over-medication. Accordingly, designs and devices have been developed to prevent free flow in infusion pumps. Although many of the free-flow prevention designs are somewhat effective, many designs suffer from arrangements that are difficult to manufacture or assemble. For example, many current pressure plate arrangements for delivery tube placement contain features which pose hard to assemble designs. Further, the components and operation of past pressure plate designs are believed to be less than optimal and leave considerable room for improvement.

Therefore, improved methods and apparatus for selectively restricting fluid flow of an infusion pump are desired, including improvements to the pressure plate.

SUMMARY OF THE INVENTION

The present invention overcomes the problems of the prior art by providing an improved device for governing fluid flow in an infusion pump. In general, fluid flow is governed through use of an attachable flow stop assembly or free flow protection device which occludes fluid flowing through an infusion pump tube, and related methods. In various embodiments, fluid flow may be restricted at the pressure plate of a reservoir cassette of an infusion pump.

One embodiment of the invention is directed to a pressure plate for attachment to an infusion pump. Specifically, the pressure plate includes a tubing support surface at least partially surrounded by a raised perimeter support comprising a raised rail and a plurality of raised supporting structures. The pressure plate also includes a plurality of guide structures extending from the raised perimeter support that define a passageway for an infusion pump tube. Additionally, in this embodiment an attachable flow stop assembly is included on the pressure plate. The attachable flow stop assembly includes an attachable occlusion arch and an attachable flow stop arm. The attachable occlusion arch includes a plurality of tab structures that attachably couple to the raised perimeter support. The occlusion arch further includes an aperture configured to surround an infusion pump tube threaded therethrough. The attachable flow stop arm is operatively coupled to the raised perimeter support adjacent the attachable occlusion arch in a spring-biased fashion such that the aperture in the occlusion arch may be selectively occluded by the flow stop arm.

Another embodiment of the present invention is directed to a cassette reservoir attachment of an infusion pump. The cassette reservoir attachment includes a reservoir housing for enclosing a quantity of fluid, an infusion tube to supply the fluid from the reservoir housing and a pressure plate. The pressure plate includes a tubing support surface for supporting a section of the infusion tube extending from the reservoir housing as well as a plurality of retention and guide features formed in the tubing support surface. The cassette reservoir attachment also includes a free flow protection device that prevents free-flow of fluid in the tube. The free flow protection device includes an attachable occlusion arch with snaps, that attach to retention and guide features, and an attachable flow stop arm, operatively coupled to the retention and guide features, for movement adjacent the attachable occlusion arch to selectively occlude an infusion tube passing through the occlusion arch.

Another embodiment of the invention is directed to an attachable flow stop assembly for use in occluding a tube of an infusion pump. The attachable flow stop assembly includes an attachable occlusion arch and an attachable flow stop arm. More specifically, the attachable occlusion arch includes tab structures to attachably couple to a pressure plate of an infusion pump and the occlusion arch defines a passageway to at least partially surround a length of an infusion pump tube. Further, the attachable flow stop arm is operatively coupled to the pressure plate for movement adjacent the attachable occlusion arch in a spring-biased fashion to selectively occlude the passageway defined by the occlusion arch.

According to an embodiment of the present invention, a method of assembling a cassette for an infusion pump is provided. The method includes providing an infusion pump reservoir cassette containing an interior reservoir bag and a top surface comprising a pressure plate. The method also includes extending an infusion tubing, coupled to the reservoir bag at a location proximate an opening in the pressure plate, through an aperture in an attachable flow stop assembly and across the surface of the pressure plate. In this embodiment, the attachable flow stop includes an attachable occlusion arch defining the aperture and having legs with one or more tab members for providing coupled engagement and an attachable flow stop arm. The method also includes securing the tab members to features in the pressure plate.

BRIEF DESCRIPTION OF THE DRAWINGS

The invention may be more completely understood in consideration of the following detailed description of various embodiments of the invention in connection with the accompanying drawings, in which.

DETAILED DESCRIPTION OF THE PREFERRED EMBODIMENTS

The invention may be embodied in other specific forms without departing from the essential attributes thereof, therefore, the illustrated embodiments should be considered in all respects as illustrative and not restrictive.

Figure 1:
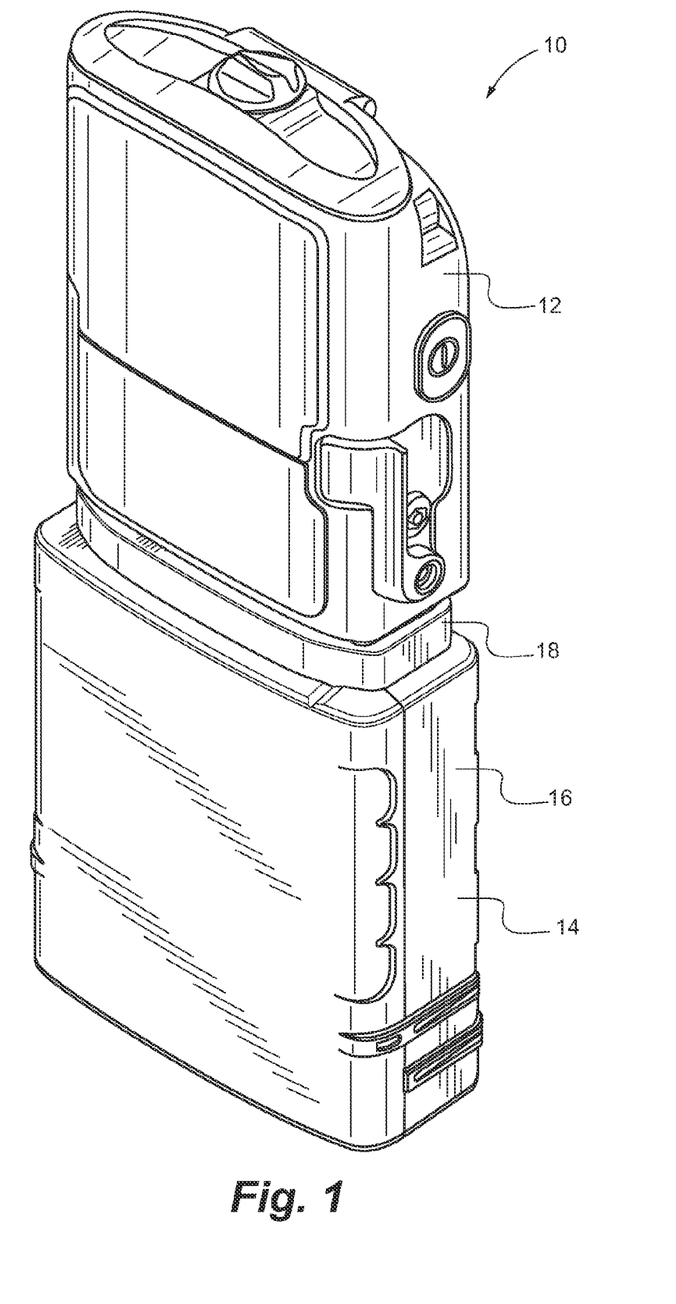
FIG. 1 is a perspective view of an assembled infusion pump arrangement, according to an embodiment of the invention.

In various embodiments of this invention an apparatus and method are disclosed for an improved flow stop device for infusion pumps. FIG. 1 generally depicts an example of an infusion pump 10 which includes a control module 12 and a cassette 14 in coupled arrangement. Specifically, the cassette 14 includes a container portion 16 which defines a space for housing and generally enclosing a bag or reservoir of medication and a pressure plate 18 extending across the upper surface of the cassette. Control module 12 and cassette 14 may be of various designs, sizes and shapes that are not limited to the sizes or types of pumps or cassettes as depicted in the figures. Infusion pumps may include peristaltic pumps, roller pumps, expulsor pumps, or other pumps. Cassettes are not limited to the large cassettes depicted in FIG. 1A and may be of any size and shape. Cassettes may be disposable or reuseable and may be sealed or able to be readily opened.

Although the flow stop device is largely set forth in this disclosure and figures as part of a cassette 14 for an infusion pump, the flow stop device should not be view as limited to implementation in such a cassette arrangement. In other embodiments, for example, the flow stop may be readily implemented in a pressure plate design for an infusion pump that is used as part of an administration set that is configured for use with an IV bag or other fluid source.

Figure 2:
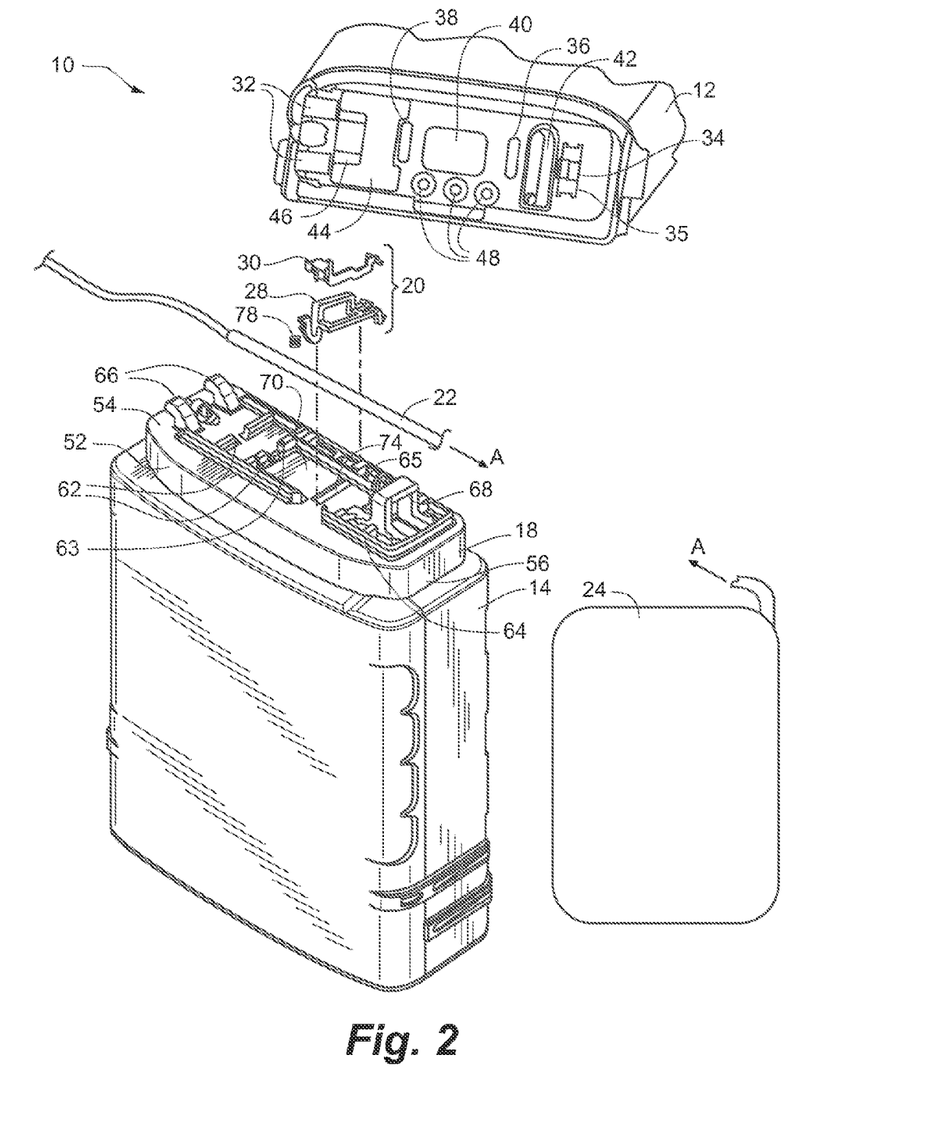
FIG. 2 is an exploded, fragmentary view of the pump assembly, according to an embodiment of the invention.

FIG. 2 illustrates an exploded view of an infusion pump, with the control module 12 and cassette 14 in a separated arrangement. More particularly, the control module 12 and cassette are depicted as independently tilted such that the components on the lower surface of the control module 12 and components on the upper surface of the pressure plate 18 are shown. A flow stop assembly 20, tubing 22, and a medication bag 24 are represented in this figure as well. In the embodiment shown, the flow stop assembly 20 includes an occlusion arch 28 and a flow stop arm 30.

The lower surface of the control module 12 includes hinge pins 32 and a latching mechanism 34 in a recess 35 that join the control module 12 and cassette 14 when the components are coupled together. The control module 12 further includes an inlet valve 36, an outlet valve 38 and a centrally located expulsor 40. Also, seen in FIG. 2 are an upstream occlusion sensor 42, a downstream occlusion sensor 44, an air detector sensor 46 and a plurality of cassette detection pins 48.

The pressure plate 18 shown in FIG. 2 includes a top and bottom surface, two side walls 52 as well as an upstream wall 54 and a downstream wall 56. The cassette 14 includes a source of fluid contained within a bag 24 or a syringe (not shown). The bag 24 or other fluid reservoir may also be positioned remote from the control module 12 and pressure plate 14. Pressure plate 18 includes a plurality of guides 62 positioned on the top of pressure plate 18 which keep tube 22 in place on pressure plate 18. Located intermediate at least one pair of guides 62 is a ramp platform 63 for providing the correct height to a passing tube 22. Pressure plate 18 also includes a rail 64 and various supporting structures 65 which surround pressure plate 18.

As shown in the figures, pressure plate 18 attaches to the control module 12 with hooks 66 and loop 68. In particular, hooks 66 engage pins 32 of the control module 12, and loop 68 is received within recess 35. Recess 35 includes a latch 34 which selectively engages loop 68 to lock pressure plate 18 to the control module 12. When pressure plate 18 is locked to control module 12, tube 22 is continually engaged by at least one of valves and expulsor features 36, 38, and 40 such that the tube 22 is constantly occluded. When in operation, the valves and expulsor selectively squeeze tube 22 against pressure plate 18 to effect the movement of fluid through tube 22.

Also shown in FIG. 2 is flow stop assembly 20, made up of flow stop occlusion arch 28 and flow stop arm 30. Although not shown assembled into the pressure plate 18 in FIG. 2, the flow stop assembly 20 can be understood as being adapted for assembly into the pressure plate 18 between the loop 68 and the central tubing support surface 70. The occlusion arch 28 is attachable to the pressure plate as it is adapted with snaps to secure into the features of the rail 64 and/or support structures 65 surrounding the center of the base plate 18.

Located adjacent the occlusion arch 28 is a recessed area 74 and features that allow for integration of a flow stop assembly 20. The flow stop arm 30 is spring biased via spring 78 and generally extends partially across the opening provided by the occlusion arch 28. The purpose of the integrated flow stop assembly 20 is to reduce the risk of medication free flow. In general, the flow stop assembly 20 is able to accomplish this by spring-biased pressure contact of the flow stop arm 30 against the tubing 22 passing through the occlusion arch 28. In other words, the flow stop arm 30 is biased such that the opening of the occlusion arch 28 is reduced so that the tubing passing through is interfered with and occluded. This will be shown and described in greater detail in connection with the subsequent figures of the application.

Figure 3:
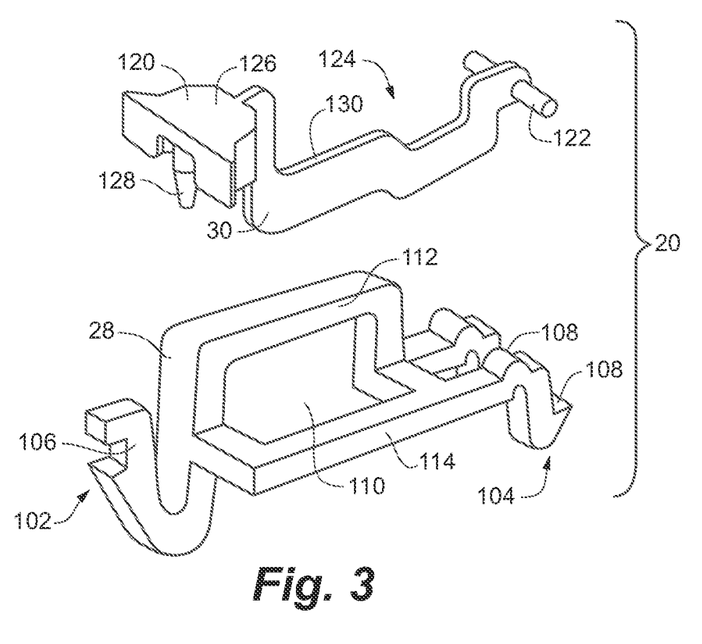
FIG. 3 is an exploded view of flow stop assembly components, according to an embodiment of the invention.

FIG. 3 is an exploded view of an embodiment of a flow stop assembly 20. The assembly allows for selectively occluding the tubing of an infusion pump and includes a flow stop occlusion arch 28 and a flow stop arm 30.

Figure 4:
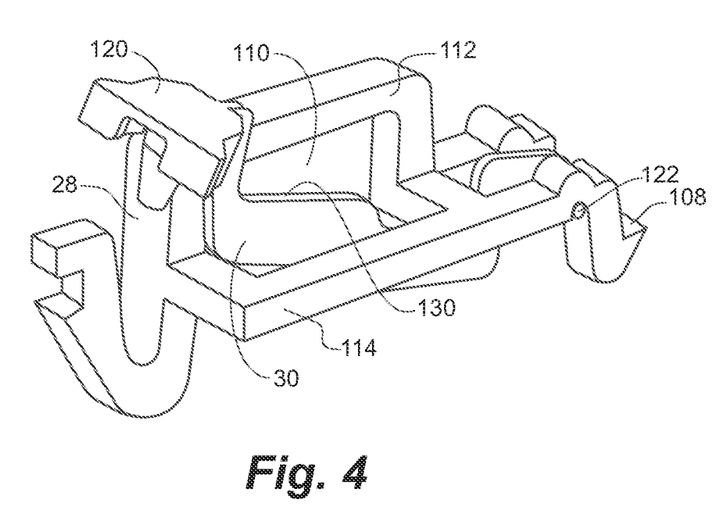
FIG. 4 depicts the flow stop assembly components of FIG. 3 coupled together in an assembled fashion, according to an embodiment of the invention.

The flow stop occlusion arch 28 is a multi-directional, elongate structure having a first end 102 and a second end 104. The first end 102 shown in FIGS. 3 and 4 has a tab retention feature 106 for coupling to the raised rail 64 or corresponding supporting structures of the pressure plate 18. The second end 104 has tab structures 108 enabling the occlusion arch to clip beneath or within retention features found on the raised rail 64 or adjacent supporting structures. Defined between the first and second ends 102 and 104 of the occlusion arch 28 is an aperature 110. This aperture 110 is shaped to surround an inserted infusion tube 22, for an infusion pump, that may be threaded therethrough when in use. The arch 28 has both an upwardly projecting portion 112 that forms a portion of the aperture 110 as well as an outwardly projecting portion 114 that forms a surrounding portion of the aperature 110 as well. The flow stop occlusion arch 28 is particularly advantageous as it is independently attachable and may remain detached from the pump for an initial portion of time when assembling the cassette, including when one is situating the tubing 22.

The flow stop arm 30 is a multi-directional body having a push tab 120 at one end and a pivoting pin 122 at the other end. The intermediate body portion 124 of the arm 30 is narrow in its width and extends in a multi-tiered fashion. The push tab 120 generally has a small flat top surface 126 of converging shape. The bottom of the push tab 120 includes a conical protrusion 128 axially receivable within a spring member 78. Accordingly, a user can press vertically downward against the top surface 126 of the push tab 120 against the bias of the spring 78 to displace the flow stop arm when in operation. As depicted in FIG. 3, the pivoting pins 122 extend horizontally from the sides of the flow stop arm 30 at the opposite end of the arm from the push tab 120. The pins 122 are shaped for placement and pivotal coupling in the concave arcuate surfaces 130 near the second end 104 of the occlusion arch 28. Further, when assembled, the body portion 124 of the arm 30 is placed through the aperture 110 formed by the arch 28. This arrangement causes the top surface 130 of the body of the arm to define the lower opening of a passageway through the aperture 110 of the occlusion arch 28. Accordingly, depression of the flow stop arm 30 will provide a greater opening through which an infusion tube 22 can pass. Release of the arm 30 will result in an upward movement of the arm 30 and upper surface 130 to provide a smaller passageway for an inserted infusion tube and will accordingly result in occlusion of the tube when the arm 30 is not being depressed. This arrangement is illustrated more fully in the assembled view of the flow stop assembly in FIG. 4.

Figure 5A:
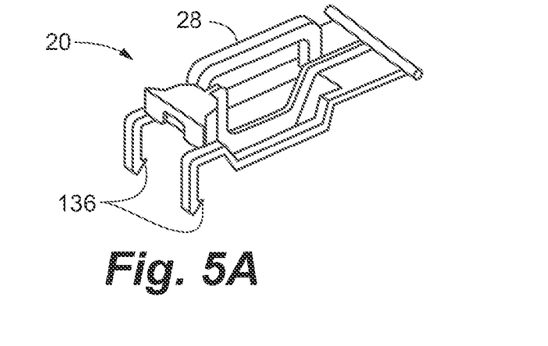
FIG. 5A is a perspective view of an embodiment of flow stop assembly components coupled together in an assembled fashion, according to an embodiment of the invention.

FIG. 5A illustrates generally an alternate assembled view of an embodiment of flow stop assembly 20 coupled together in an assembled fashion. In this embodiment the first end of the occlusion arch 28 has alternate tabs 136 for snapping into the pressure plate rail 64 and supporting structures.

Figure 5B:
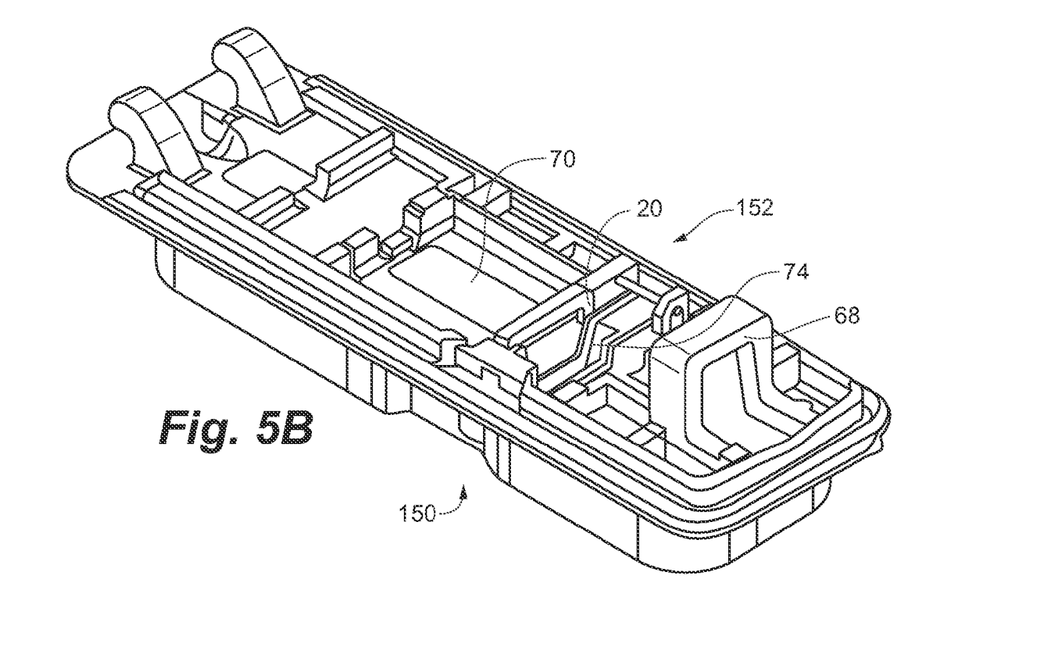
FIG. 5B is a perspective view of a pressure plate including the flow stop assembly components of FIG. 5A, according to an embodiment of the invention.

FIG. 5B illustrates the flow stop assembly of FIG. 5A inserted into a pressure plate 18. In general, the flow stop assembly extends horizontally across the pressure plate 18 of the pump from the front of the pump to the back of the pump with one end located proximate the rail 64 on side 150 and the other end of the assembly proximate the rail 64 and supporting structures on the other side 152. Further, the flow stop assembly 20 generally rests within a vertically recessed slot 74 within the pressure plate 18. The recess 74 traverses the pump from front side 150 to back side 152 and is located between the between the loop 68 and the central tubing support surface 70.

Figure 6:
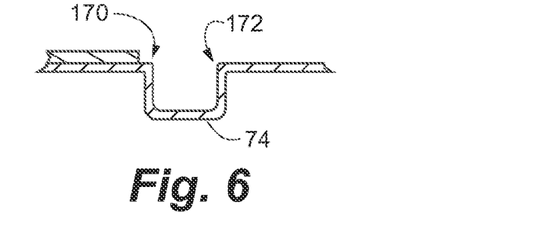
FIG. 6 is a cross-sectional view of a pressure plate recess for placement of a flow stop insert, according to an embodiment of the invention.

FIG. 6 is a cross-sectional view of the recess 74 of the pressure plate 18 in which the flow stop assembly 20 is placed during manufacture and assembly of the cassette 14 or pressure plate 18. Unlike some prior art designs, the recess 74 does not include ramp-like features at the edges of the pressure plate surface at locations 170 and 172, for example. By eliminating ramp-like features at these locations, the new flow stop assembly 20 does not suffer from potential unwanted back pressure effects that can impact the accuracy and desired operation of an infusion pump 10.

Figure 7A:
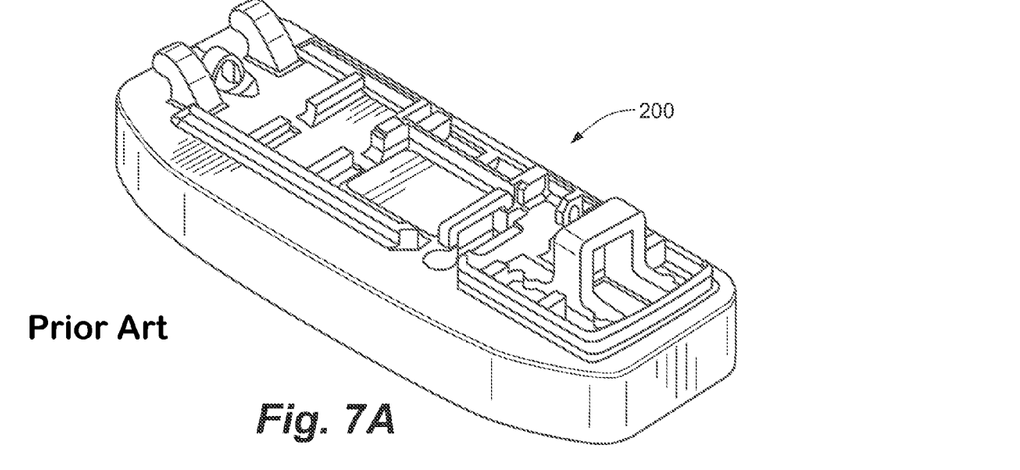
FIG. 7A is a perspective view of an exemplary pressure plate of an infusion pump assembly of the prior art.
Figure 7B:
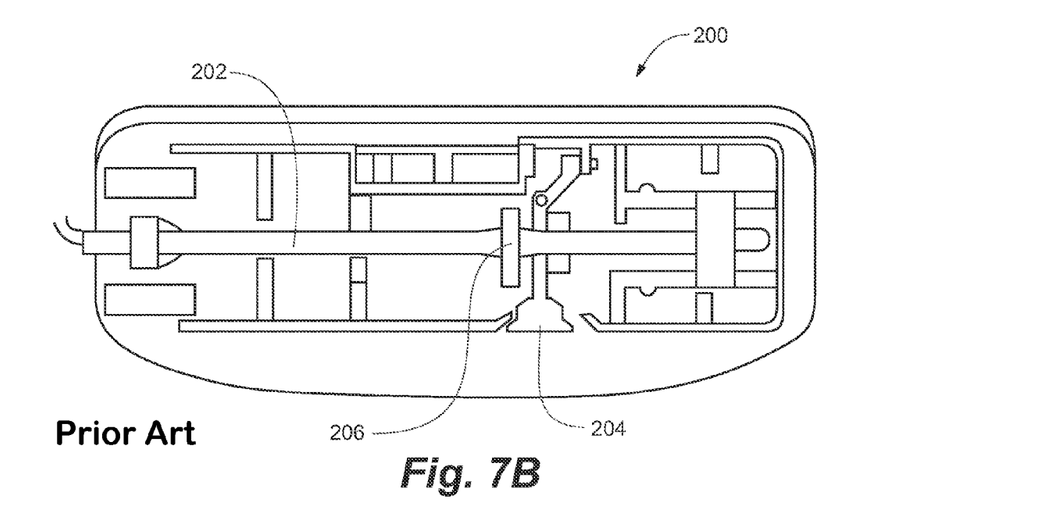
FIG. 7B is a top view of the free-flow control portions of an exemplary pressure plate of the prior art.

FIG. 7A illustrates generally a pressure plate 200 of the prior art. FIG. 7B illustrates generally a top view of an assembled pressure plate 200, infusion tubing 202 and a flow stop arm 204 of the prior art. These figures illustrate a prior art arrangement in which an occlusion arch 206 was integrally formed with the pressure plate 200. Assembling this design during manufacturing is somewhat challenging. For example, in order to assemble tubing into the configuration shown in FIG. 7B, it is necessary to thread tubing through the very narrow opening in the arch created by the spring biased flow stop arm 204. Alternatively, allowing one to thread this structure through an attachable arrangement, like that of embodiments of the present invention, greatly reduces manufacturing difficulties and substantially reduces assembly costs.

Figure 8:
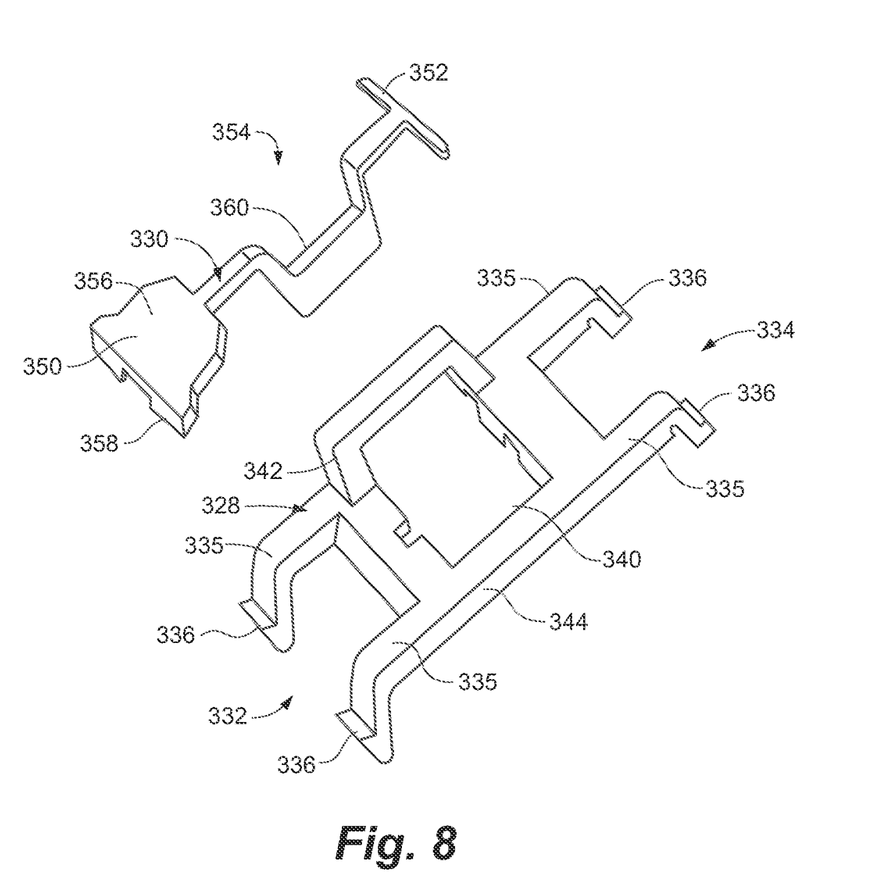
FIG. 8 is an exploded view of an alternate embodiment of a flow stop assembly, according to an embodiment of the invention.

FIG. 8 is an exploded view of an alternate embodiment of a flow stop assembly, with a flow stop occlusion arch 328 and flow stop arm 330.

The occlusion arch 328 is a structural clip having a first end 332 and a second end 334. Each of these ends has a pair of legs 335 equipped with tab retention features 336 for coupling to the raised rail or corresponding supporting structures of the pressure plate 18. The tab retention features 336 may clip beneath or within retention features found on the raised rail or adjacent supporting structures of the pressure plate 18. Located between the first and second ends 332 and 334 of the occlusion arch 328 is an aperture 340. This aperture 340 is shaped to surround an inserted infusion tube 22, for an infusion pump, that may be threaded therethrough when in use. The arch 328 has both an upwardly projecting portion 342 that forms a portion of the aperture 340 as well as an outwardly projecting portion 344 that forms a surrounding portion of the aperture 340 as well. The flow stop occlusion arch 328 is particularly advantageous as it is attachable and may initially remain detached from the pump when assembling the cassette, including situating the tubing 22.

The flow stop arm 330 is a multi-directional body having a push tab 350 at one end and a pivoting pin 352 at the other end. The intermediate body portion 354 of the arm 330 is narrow in its width and extends in a multi-tiered fashion. The push tab 350 generally has a small flat top surface 356 of converging shape. The bottom of the push tab 350 includes a conical protrusion 358 axially receivable within a spring member 78. Accordingly, a user can press vertically downward against the top surface 356 of the push tab 350 against the bias of the spring 78 to displace the flow stop arm when in operation. The pivoting pins 352 extend horizontally from the sides of the flow stop arm 330 at the opposite end of the arm from the push tab 350. The pins 352 are shaped for placement and pivotal coupling near the second end 334 of the occlusion arch 328. Further, when assembled, the body portion 354 of the arm 30 is placed through the aperture 340 formed by the arch 342. This arrangement causes the top surface 360 of the body of the arm 330 to define the lower opening of a passageway through the aperture 340 of the occlusion arch 328. Accordingly, depression of the flow stop arm 330 will provide a greater opening through which an infusion tube 22 can pass. Release of the arm 330 will result in an upward movement of the arm 330 and upper surface 360 to provide a smaller passageway for an inserted infusion tube and will accordingly result in occlusion of the tube when the arm 330 is not being depressed.

Figure 9:
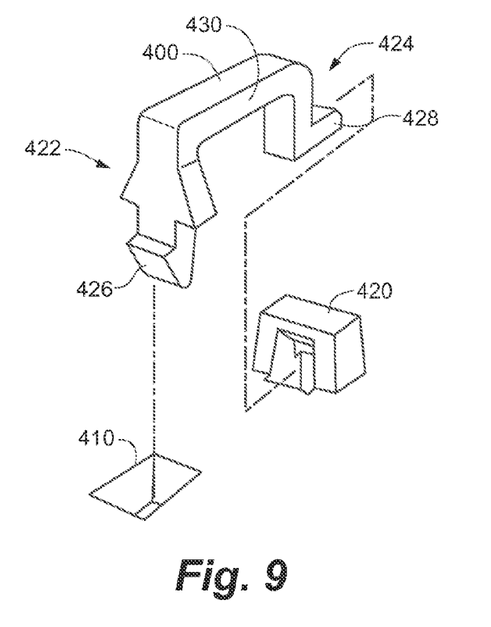
FIG. 9 is an exploded view of an alternate embodiment of a flow stop arch, according to an embodiment of the invention.

FIG. 9 depicts an alternate embodiment of a flow stop arch design. This embodiment depicts an alternate attachable flow stop arch component, occlusion arch 400, as well as retaining features 410 and 420 that would be integrated into the pressure plate 18 of such a design.

The occlusion arch 400 is a structural clip having a first end 422 and a second end 424. The first end 422 is equipped with a tab retention feature 426 for coupling to the recessed structure 410 of the pressure plate 18. The tab retention features 426 may clip beneath or within this recessed structure 410. The second end 424 includes a protrusion 428 that extends slightly in a horizontally disposed direction. This protrusion 428 may be aligned to fit within a retaining feature 420. A raised arch portion 430 comprises the central body of the occlusion arch 400 between the first and second ends 422 and 424. This raised arch portion 430 partially defines an aperture in its interior. When the occlusion arch 400 is inserted into the respective retaining features 410 and 420 the arch perimeter combines with the pressure plate to form an aperture into which an infusion tube 22 may be inserted and threaded therethrough. The occlusion arch could be used together with a flow stop arm in some embodiments. In other embodiments the occlusion arch operates on its own to sufficiently compress a infusion tube for occlusion.

Figure 10:
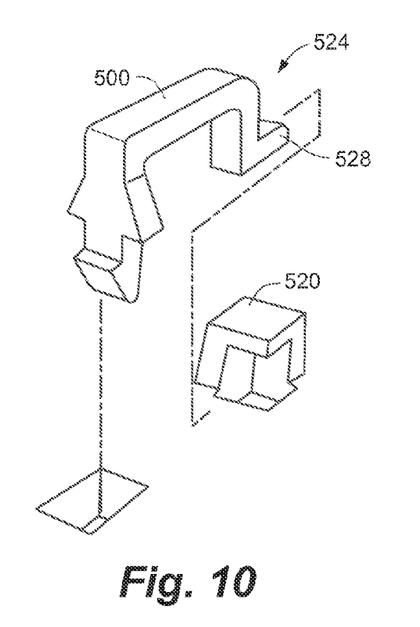
FIG. 10 is an exploded view of an alternate embodiment of a flow stop arch, according to an embodiment of the invention.

FIG. 10 depicts an alternate embodiment of a flow stop arch design. This embodiment is largely the same as the one depicted in FIG. 9, but has a slightly different retaining feature 520 from the retaining feature 420 shown in FIG. 9. Specifically, the retaining feature allows access from two sides. Accordingly, the ability to insert the protrusion 528 at the end 524 of the flow stop arch component 500 from multiple directions is enabled.

Certain embodiments may further include a sensor as part of the infusion pump that could detect the presence of the flow stop feature. This could be another sensor beyond the cassette detection pins 48 or could utilize one of the pins 48. Accordingly, the pump 12 would alarm if it did not detect the flow stop feature. This would also be beneficial in situations where the plate or housing became detached from the pump 12, since the pump would sound an alarm.

The cassette for an infusion pump may be assembled by first providing an infusion pump reservoir cassette containing an interior reservoir bag and a top surface comprising a pressure plate. This method further includes extending an infusion tubing, coupled to the reservoir bag at a location proximate an opening in the pressure plate, through an aperture in an attachable flow stop assembly and across the surface of the pressure plate. The attachable flow stop includes an attachable occlusion arch and an attachable flow stop arm. The attachable flow stop defines the aperture, and has legs with one or more tab members for providing coupled engagement and an attachable flow stop arm. The method further includes securing the tab members to features in the pressure plate.

It should also be appreciated that the exemplary embodiment or exemplary embodiments are only examples, and are not intended to limit the scope, applicability, or configuration of the invention in any way. Rather, the foregoing detailed description will provide those skilled in the art with an enabling disclosure for implementing the exemplary embodiment or exemplary embodiments. It should be understood that various changes can be made in the function and arrangement of elements without departing from the scope of the invention as set forth in the appended claims and the legal equivalents thereof.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A pressure plate for attachment to an infusion pump, comprising:
   a tubing support surface at least partially surrounded by a raised perimeter support comprising a raised rail and a plurality of raised supporting structures;
   a plurality of guide structures extending from the raised perimeter support that define a passageway for an infusion pump tube; and
   an attachable flow stop assembly, including:
      an attachable occlusion arch including a plurality of tab structures that attachably couple to the raised perimeter support, the occlusion arch further including an aperture configured to surround an infusion pump tube threaded therethrough; and
      an attachable flow stop arm operatively coupled to the raised perimeter support adjacent the attachable occlusion arch in a spring-biased fashion such that the aperture in the occlusion arch may be selectively occluded by the flow stop arm.

2. The pressure plate of claim 1, wherein the attachable flow stop is adapted to provide flow stop detection features to a sensor on the infusion pump.

3. The pressure plate of claim 1, further including a ramp feature on the tubing support surface proximate the passageway for the infusion pump tube to align the height of the infusion pump tube.

4. The pressure plate of claim 1, wherein positive stops are provided to retain infusion pump tubing to the tubing support surface.

5. The pressure plate of claim 1, wherein the attachable occlusion arch includes four tab structures.

6. The pressure plate of claim 1, wherein the attachable occlusion arch includes three tab structures.

7. The pressure plate of claim 1, wherein the raised perimeter support includes recesses in the tubing support surface for retention of the tab structures.

8. A cassette reservoir attachment of an infusion pump, comprising:
   a reservoir housing for enclosing a quantity of fluid;
   an infusion tube to supply the fluid from the reservoir housing;
   a pressure plate including:
      a tubing support surface for supporting a section of the infusion tube extending from the reservoir housing;
      a plurality of retention and guide features formed in the tubing support surface;

a free flow protection device that prevents free-flow of fluid in the tube, including:
- an attachable occlusion arch with snaps that attach to retention and guide features; and
- an attachable flow stop arm operatively coupled to the retention and guide features for movement adjacent the attachable occlusion arch to selectively occlude an infusion tube passing through the occlusion arch.

9. A cassette reservoir attachment of claim 8, wherein the reservoir housing is configured for enclosing the quantity of fluid in a bag in the reservoir housing.

10. An attachable flow stop assembly for use in occluding a tube of an infusion pump, comprising:
- an attachable occlusion arch including tab structures to attachably couple to a pressure plate of an infusion pump, the occlusion arch defining a passageway to at least partially surround a length of an infusion pump tube; and
- an attachable flow stop arm operatively coupled to the pressure plate for movement adjacent the attachable occlusion arch in a spring biased fashion to selectively occlude the passageway defined by the occlusion arch.

11. The attachable flow stop of claim 10, wherein the attachable occlusion arch includes four tab structures.

12. The attachable flow stop of claim 10, wherein the attachable occlusion arch includes three tab structures.

13. The attachable flow stop of claim 10, wherein the attachable occlusion arch contains an aperture completely surrounding a length of an infusion pump tube.

14. The attachable flow stop of claim 10, wherein the attachable occlusion arch partially defines aperture passageway.

* * * * *